United States Patent
Betancourt-Villamizar et al.

(10) Patent No.: US 10,869,852 B2
(45) Date of Patent: Dec. 22, 2020

(54) COMPOSITION AND METHOD FOR TREATMENT OF NEURODEGENERATIVE DISEASES

(71) Applicant: TEAM FOODS COLOMBIA S.A., Bogotá (CO)

(72) Inventors: Eddy C. Betancourt-Villamizar, Bogotá (CO); Juan Murcillo-Rojas, Bogotá (CO); Ruben Betancourt-Cortes, Bogotá (CO)

(73) Assignee: Team Foods Colombia S.A., Bogota (CO)

( * ) Notice: Subject to any disclaimer, the term of this patent is extended or adjusted under 35 U.S.C. 154(b) by 0 days.

(21) Appl. No.: 16/129,580

(22) Filed: Sep. 12, 2018

(65) Prior Publication Data
US 2019/0076387 A1    Mar. 14, 2019

Related U.S. Application Data

(63) Continuation of application No. PCT/IB2017/000337, filed on Mar. 14, 2017.

(60) Provisional application No. 62/307,714, filed on Mar. 14, 2016.

(51) Int. Cl.
| | |
|---|---|
| *A61K 36/00* | (2006.01) |
| *A61K 31/23* | (2006.01) |
| *A61K 31/355* | (2006.01) |
| *A61K 31/365* | (2006.01) |
| *A61K 31/4188* | (2006.01) |
| *A61K 31/685* | (2006.01) |
| *A61K 36/53* | (2006.01) |
| *A61K 36/63* | (2006.01) |
| *A61K 31/519* | (2006.01) |
| *A61K 31/22* | (2006.01) |
| *A61P 25/28* | (2006.01) |
| *A61K 9/00* | (2006.01) |

(52) U.S. Cl.
CPC ............ *A61K 31/23* (2013.01); *A61K 9/0053* (2013.01); *A61K 31/22* (2013.01); *A61K 31/355* (2013.01); *A61K 31/365* (2013.01); *A61K 31/4188* (2013.01); *A61K 31/519* (2013.01); *A61K 31/685* (2013.01); *A61K 36/53* (2013.01); *A61K 36/63* (2013.01); *A61P 25/28* (2018.01)

(58) Field of Classification Search
CPC ...................................................... A61K 36/00
USPC ........................................................ 424/725
See application file for complete search history.

(56) References Cited

U.S. PATENT DOCUMENTS

| | | | |
|---|---|---|---|
| 6,835,750 B1 | 12/2004 | Henderson | |
| 2003/0232422 A1* | 12/2003 | Gerber | C12N 1/20 435/252.1 |
| 2013/0017278 A1 | 1/2013 | Keller | |

FOREIGN PATENT DOCUMENTS

WO          03002133 A2     1/2003

OTHER PUBLICATIONS

Volz H P et al "[Improvement in quality of life in the elderly. Results of a placebo-controlled study on the efficacy and tolerability of lecithin fluid in patients with impaired cognitive functions].", MMW Fortschritte Der Medizin Dec. 9, 2004, vol. 146, No. Suppl 3-4, 9 Dec. 2004 (Dec. 9, 2004), pp. 99-106, XP009195075.
Valls-Pedret Cinta et al. "Mediterranean Diet and Age-Related Cognitive Decline a Randomized Clinical Trial", JAMA Internal Medicine, vol. 175, No. 7, Jul. 2015 (Jul. 1, 2015), pp. 1094-1103, XP009195074.
International Search Report and Written Opinion issued in PCT/IB2017/000337, dated Aug. 9, 2017.

* cited by examiner

*Primary Examiner* — Michael V Meller
(74) *Attorney, Agent, or Firm* — BakerHostetler (57) ABSTRACT

The present invention, in embodiments, is a composition and method of treatment using a composition that includes: a first component comprising: 75 to 97 weight percent of medium chain triglycerides; wherein the medium chain triglycerides comprise 6 to 12 carbon fatty acid esters of glycerol; 4 to 15 weight percent of soy lecithin; 0.05 to 1 weight percent of biotin; and 0.01 to 0.2 weight percent of antioxidant, and olive oil, wherein the antioxidant is selected from the group consisting of tocopherol, ascorbyl palmitate, Rosemary extract and mixtures thereof.

4 Claims, 7 Drawing Sheets

| | | | |
|---|---|---|---|
| Monoinsaturadas / Monounsaturated | 10.78 | 77 | g |
| Poliinsaturadas / Poliunsaturated | 1.26 | 9 | g |
| COLESTEROL / CHOLESTEROL | 0 | 0 | mg |
| Vitamina E / Vitamin E | 2.8 | 20 | mg |

1.4. Ingredientes

Aceite Oliva Virgen Extra variedad Arbequina con un mayor porcentaje de virgen extra variedad Picual

1.4. Ingredients

Extra Virgin Olive Oil Arbequina variety with a higher percentage of Picual variety

1.5. Condiciones de uso

Apto para consumir de modo directo.

Para evitar posibles alteraciones y disfrutar plenamente de las cualidades de este alimento conviene tener en cuenta una serie de recomendaciones:

- Debe evitarse que le dé directamente la luz solar o una luz artificial fuerte, así como la cercanía a fuentes de calor. Su conservación en un lugar fresco y al amparo de la luz puede garantizar la calidad del producto durante mucho tiempo.
- Conviene tapar bien el envase después de su consumo y mantenerla en un lugar reservado, a salvo de olores extraños que le puedan transmitir otros alimentos, ya que los absorbe fácilmente.

1.5. Use conditions

Ready to be consumed directly.

To avoid possible alterations and fully enjoy the qualities of this food the following recommendations should be followed:

-Avoid direct sun light or strong artificial light as well as heat sources. Its preservation in a cool place protected from light can guarantee its quality for long periods of time. It is advisable to close the bottle after use and keep it in a reserved place away from off odours from other foodstuff since it can absorb them easily.

1.6. Características Organolépticas

Normales, con aromas propios y características sin acusar síntomas de rancidez, alteración o contaminación.

Aroma afrutado característico de las aceitunas, medianamente picante.

Color verde amarillento.

1.6. Organoleptic Characteristic

Normal, with own aromas and characteristic without accusing symptoms of rancidity, alteration or contamination.

Distinctive fruity aroma, characteristic of olives, peppery aftertaste.

Medium yellow-green in color

1.7. Características Físico-Químicas / Physical-Chemical Characteristic

COMPOSITION AND METHOD FOR TREATMENT OF NEURODEGENERATIVE DISEASES

RELATED APPLICATION

This application is a continuation of International patent application PCT/M2017/000337, filed on Mar. 14, 2017, entitled "COMPOSITION AND METHOD FOR TREATMENT OF COGNITIVE IMPAIRMENT" which claims the priority of U.S. provisional application Ser. No. 62/307,714, entitled "COMPOSITION FOR TREATMENT OF NEURODEGENERATIVE DISEASES," filed Mar. 14, 2016, which are both incorporated herein by reference in their entirety for all purposes.

BACKGROUND OF INVENTION

Neurodegenerative diseases are known.

TECHNICAL FIELD

The present invention relates to compositions for treatment of neurodegenerative disease.

BRIEF SUMMARY OF INVENTION

In embodiments, the present invention is a composition that includes: 75 to 97 weight percent of medium chain triglycerides; wherein the medium chain triglycerides comprise 6 to 12 carbon fatty acid esters of glycerol; 4 to 15 weight percent of soy lecithin; 0.05 to 1 weight percent of biotin; and 0.01 to 0.2 weight percent of antioxidant, wherein the antioxidant is selected from the group consisting of tocopherol, ascorbyl palmitate, Rosemary extract and mixtures thereof.

In embodiments, the composition includes 85 to 97 weight percent of the medium chain triglycerides. In yet other embodiments, the composition includes 8 to 15 weight percent of the soy lecithin. In other embodiments, the composition includes 1 weight percent of the biotin.

In another embodiment, the composition includes 0.1 to 0.2 weight percent of the antioxidant. In yet other embodiments, the composition further includes 0.05 weight percent to 0.11 weight percent of folic acid.

In yet other embodiments, the composition includes: 85 to 97 weight percent of medium chain triglycerides; wherein the medium chain triglycerides comprise 6 to 12 carbon acid esters of glycerol; 5 to 10 weight percent of soy lecithin; 0.05 to 0.2 weight percent of biotin; and 0.01 to 0.2 weight percent of antioxidant, wherein the antioxidant is selected from the group consisting of tocopherol, ascorbyl palmitate, Rosemary extract and mixtures thereof. In still other embodiments, the composition further includes 0.05 to 0.1 weight percent of pyridoxine and/or cobalamin.

In other embodiments, the present invention is a method of treatment and/or prevention of cognitive impairment including: orally administering an effective amount per day to a human in need thereof of a composition to improve a clinical dementia rating of the human at least 5% measured after a 12 month duration when compared to a human that is orally administered an identical amount to the effective amount per day of olive oil for a 12 month duration; wherein the composition includes: 75 to 97 weight percent of medium chain triglycerides; wherein the medium chain triglycerides comprise 6 to 12 carbon acid esters of glycerol; and 4 to 15 weight percent of soy lecithin.

In yet other embodiments, the effective amount includes 15 to 25 grams per dose and two to four doses per day. In embodiments, the effective amount includes 15 grams per dose and three to four doses per day. In other embodiments, the effective amount includes 17 grams per dose and three doses per day.

In yet other embodiments, the effective amount includes 50 grams per day. In embodiments, the method of treatment and/or prevention includes a composition that further includes at least one of: 0.05 to 1 weight percent of biotin or 0.01 to 0.2 weight percent of antioxidant. In embodiments, the composition includes an antioxidant is selected from the group consisting of tocopherol, ascorbyl palmitate, Rosemary extract and mixtures thereof.

In yet other embodiments, the present invention is a method of treatment and/or prevention of cognitive impairment including: orally administering an effective amount per day to a human in need thereof of a composition to improve a clinical dementia rating of the human at least 25% measured after a 12 month duration when compared to a human that is orally administered an identical amount to the effective amount per day of olive oil for a 12 month duration; wherein the composition includes: a first component comprising: 75 to 97 weight percent of medium chain triglycerides; wherein the medium chain triglycerides comprise 6 to 12 carbon acid esters of glycerol; 4 to 15 weight percent of soy lecithin; and olive oil.

In embodiments, a weight ratio of the first component to the olive oil is 2:1 to 1:2. In yet other embodiments, the weight ratio of the first component to the olive oil is 1:1.

In embodiments, the effective amount comprises 15 to 25 grams per dose and two to four doses per day. In yet other embodiments, the effective amount comprises 15 grams per dose and three to four doses per day. In yet other embodiments, the effective amount comprises 17 grams per dose and three doses per day and the weight ratio of the first component to the olive oil is 2:1 to 1:2.

In embodiments, the method includes a composition that further includes at least one of: 0.05 to 1 weight percent of biotin or 0.01 to 0.2 weight percent of antioxidant. In yet other embodiments, the antioxidant is selected from the group consisting of tocopherol, ascorbyl palmitate, Rosemary extract and mixtures thereof.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on.

As used herein, the term "clinical dementia rating" or "CDR" is used to determine the "treatment of cognitive impairment." CDR is a global assessment instrument used in clinical trials and longitudinal research projects to rate the presence and severity of cognitive problems in Alzheimer disease and related disorders. The CDR rates the severity of Alzheimer disease using a 5-point scale that rates the severity of signs and symptoms as they affect the patient's ability to function in the 6 cognitive categories of memory, orientation, judgment and problem solving, community affairs/involvement, home life and hobbies, and personal care. Although designed for use with patients with a probable diagnosis of AD, the CDR is appropriate for use in the assessment of dementia that is associated with other medical disorders (e.g., Lewy body disease). The CDR rating varies as follows:

0=Normal
0.5=Very Mild Dementia
1=Mild Dementia
2=Moderate Dementia
3=Severe Dementia The CDR is completed by the researcher or a clinician after performing a face-to-face, semi-structured interview with the patient and a reliable informant such as a spouse or other family member/caregiver. The informant is interviewed first, and the results of that interview are used to assess patient recall of events and to confirm the accuracy of patient responses. In each cognitive category the patient receives a score of 0 (no cognitive impairment) to 3 (severe cognitive impairment). The CDR can be scored to obtain a global score by using an algorithm that weights memory more heavily than the other categories, or it can be scored using the sum of boxes (SOB) method in which all categories are weighted equally; in general, the higher the score, the greater the severity of dementia The CDR can be administered and interpreted in any setting in which a patient requires evaluation or treatment for AD or other dementia, including inpatient and outpatient healthcare settings and community settings (e.g., during provision of in-home care by a home health nurse; as part of a public health screening program)

The CDR is administered and interpreted by trained healthcare clinicians who provide treatment to patients with suspected or known dementia and/or medical conditions that are known to correspond with dementia based, at least in part, on the information in Table 1 below:

TABLE 1

| | Clinical Dementia Rating: (CDR) | | | | |
|---|---|---|---|---|---|
| | 0 | 0.5 | 1 | 2 | 3 |
| | | | Impairment | | |
| | None | Questionable | Mild | Moderate | Severe |
| | 0 | .5 | 1 | 2 | 3 |
| Memory | No memory loss or slight inconsistent forgetfulness | Consistence slight forgetfulness; partial recollection of events; "benign" forgetfulness | Moderate memory loss; more marked for recent events; defect interferes with everyday activities | Severe memory loss; only highly learned material retained; new material rapidly lost | Severe memory loss; only fragments remain |

TABLE 1-continued

Clinical Dementia Rating: (CDR)

| | 0 | 0.5 | 1 | 2 | 3 |
|---|---|---|---|---|---|
| | | | Impairment | | |
| | None 0 | Questionable .5 | Mild 1 | Moderate 2 | Severe 3 |
| Orientation | Fully orientated | Fully orientated except for slight difficulty with time relationships | Moderate difficulty with time relationships; orientated for place at examination; may have geographic disorientation elsewhere | Severe difficulty with time relationships; usually disorientated to time; often to place | Orientated to person only |
| Judgment & Problem Solving | Solve everyday problems & handles business & financial affairs well; judgment good in relation to past performance | Slight impairment in solving problems, similarities and differences | Moderate difficulty in handling problems, similarities, and differences; social judgment usually maintained | Severely impaired in handling problems, similarities and differences; social judgment usually impaired | Unable to make judgments or solve problems |
| Community Affairs | Independent function at usual level in job, shopping, volunteer and social groups | Slight impairment in these activities | Unable to function independently at these activities although may still be engaged in some; appears normal to casual inspection | No pretense of independent function outside of home. Appears well enough to be taken to functions outside a family home | Appears too ill to be taken to functions outside a family home |
| Home and Hobbies | Life at home, hobbies, and intellectual interests well maintained | Life at home, hobbies, and intellectual interests slightly impaired | Mild but definite impairment of function at home; more difficult chores abandoned; more complicated hobbies and interests abandoned | Only simple chores preserved; very restricted interests, poorly maintained | No significant function in home |
| Personal care | | Fully capable of self-care | Needs prompting | Requires assistance in dressing, hygiene, keeping of personal effects | Requires much help with personal care; frequent incontinence |

Score only as declined from previous usual level due to cognitive loss, not impairment due to other factors.

As used herein, the term "olive oil" means a lipid pressed from ripe olives. A non-limiting example of olive oil according to the present invention is shown in FIGS. 4 to 7.

As used herein, the term "Lipidbrain" corresponds to an embodiment of a lipidic blend of the present invention.

In embodiments, the present invention is a composition that includes: 75 to 97 weight percent of medium chain triglycerides; wherein the medium chain triglycerides comprise 6 to 12 carbon acid esters of glycerol; 4 to 15 weight percent of soy lecithin; 0.05 to 1 weight percent of biotin; and 0.01 to 0.2 weight percent of antioxidant, wherein the antioxidant is selected from the group consisting of tocopherol, ascorbyl palmitate, Rosemary extract and mixtures thereof.

In embodiments, the composition includes 85 to 97 weight percent of the medium chain triglycerides. In yet other embodiments, the composition includes 8 to 15 weight percent of the soy lecithin. In other embodiments, the composition includes 1 weight percent of the biotin.

In another embodiment, the composition includes 0.1 to 0.2 weight percent of the antioxidant. In yet other embodiments, the composition further includes 0.05 weight percent to 0.11 weight percent of folic acid.

In yet other embodiments, the composition includes: 85 to 97 weight percent of medium chain triglycerides; wherein the medium chain triglycerides comprise 6 to 12 carbon fatty acid esters of glycerol; 5 to 10 weight percent of soy lecithin; 0.05 to 0.2 weight percent of biotin; and 0.01 to 0.2 weight percent of antioxidant, wherein the antioxidant is selected from the group consisting of tocopherol, ascorbyl palmitate, Rosemary extract and mixtures thereof.

In other embodiments, the present invention is a method of treatment and/or prevention of cognitive impairment including: orally administering an effective amount per day to a human in need thereof of a composition to improve a clinical dementia rating of the human at least 5% measured after a 12 month duration when compared to a human that is orally administered an identical amount to the effective amount per day of olive oil for a 12 month duration; wherein the composition includes: 75 to 97 weight percent of medium chain triglycerides; wherein the medium chain triglycerides comprise 6 to 12 carbon acid esters of glycerol; and 4 to 15 weight percent of soy lecithin.

In yet other embodiments, the effective amount includes 15 to 25 grams per dose and two to four doses per day. In embodiments, the effective amount includes 15 grams per dose and three to four doses per day. In other embodiments, the effective amount includes 17 grams per dose and three doses per day.

In yet other embodiments, the effective amount includes 50 grams per day. In embodiments, the method of treatment and/or prevention includes a composition that further includes at least one of: 0.05 to 1 weight percent of biotin or 0.01 to 0.2 weight percent of antioxidant. In embodiments, the composition includes an antioxidant is selected from the group consisting of tocopherol, ascorbyl palmitate, Rosemary extract and mixtures thereof.

In yet other embodiments, the present invention is a method of treatment and/or prevention of cognitive impairment including: orally administering an effective amount per day to a human in need thereof of a composition to improve a clinical dementia rating of the human at least 25% measured after a 12 month duration when compared to a human that is orally administered an identical amount to the effective amount per day of olive oil for a 12 month duration; wherein the composition includes: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil.

In embodiments, a weight ratio of the first component to the olive oil is 2:1 to 1:2. In yet other embodiments, the weight ratio of the first component to the olive oil is 1:1.

In embodiments, the effective amount comprises 15 to 25 grams per dose and two to four doses per day. In yet other embodiments, the effective amount comprises 15 grams per dose and three to four doses per day. In yet other embodiments, the effective amount comprises 17 grams per dose and three doses per day and the weight ratio of the first component to the olive oil is 2:1 to 1:2.

In embodiments, the method includes a composition that further includes at least one of: 0.05 to 1 weight percent of biotin or 0.01 to 0.2 weight percent of antioxidant. In yet other embodiments, the antioxidant is selected from the group consisting of tocopherol, ascorbyl palmitate, Rosemary extract and mixtures thereof.

In some embodiments, the present invention is a method of treatment and/or prevention of neurodegenerative disease comprising orally administering an effective amount of a composition to a human of a composition to reduce a rate of onset or magnitude of the neurodegenerative disease when compared to a human administered olive oil alone.

In some embodiments, the cognitive impairment is a result of a neurodegenerative disease including, but not limited to, Very Mild Dementia, Mild Dementia, Moderate Dementia, Severe Dementia, Alzheimer's Disease, progressive supranuclear palsy; a dementia; Creutzfeldt-Jacob disease, frontotemporal dementia, Pick's disease, Frontotemporal Dementia with Parkinsonism-17 corticobasal degeneration, frontotemporal lobe degeneration; Huntington's Disease; or Parkinson's Disease.

In some embodiments, the present invention is a composition that may be used for the treatment and/or prevention of neurodegenerative disease. In some embodiments, the composition is a lipidic blend. In some embodiments, the composition can be taken by a subject to improve memory, cognitive performance, and concentration, and could be used as a treatment for or a preventative against neurodegenerative diseases, including Alzheimer's disease.

In some embodiments, the present invention is a composition, comprising: 75 to 97 weight percent of medium chain triglycerides. In some embodiments, the present invention is a composition, comprising: 75 to 90 weight percent of medium chain triglycerides. In some embodiments, the present invention is a composition, comprising: 75 to 85 weight percent of medium chain triglycerides. In some embodiments, the present invention is a composition, comprising: 75 to 80 weight percent of medium chain triglycerides. In some embodiments, the present invention is a composition, comprising: 80 to 97 weight percent of medium chain triglycerides. In some embodiments, the present invention is a composition, comprising: 85 to 97 weight percent of medium chain triglycerides. In some embodiments, the present invention is a composition, comprising: 90 to 97 weight percent of medium chain triglycerides. In some embodiments, the present invention is a composition, comprising: 80 to 90 weight percent of medium chain triglycerides.

In some embodiments, the medium chain triglycerides comprise 6 to 12 carbon fatty acid esters of glycerol. In some embodiments, the medium chain triglycerides comprise 6 to 10 carbon fatty acid esters of glycerol. In some embodiments, the medium chain triglycerides comprise 6 to 8 carbon fatty acid esters of glycerol. In some embodiments, the medium chain triglycerides comprise 8 to 12 carbon fatty acid esters of glycerol. In some embodiments, the medium chain triglycerides comprise 10 to 12 carbon fatty acid esters of glycerol. In some embodiments, the medium chain triglycerides comprise 8 to 10 carbon fatty acid esters of glycerol.

In some embodiments, the composition comprises 4 to 15 weight percent of lecithin. In some embodiments, the composition comprises 4 to 13 weight percent of lecithin. In some embodiments, the composition comprises 4 to 11 weight percent of lecithin. In some embodiments, the composition comprises 4 to 9 weight percent of lecithin. In some embodiments, the composition comprises 4 to 7 weight percent of lecithin. In some embodiments, the composition comprises 4 to 5 weight percent of lecithin. In some embodiments, the composition comprises 6 to 15 weight percent of lecithin. In some embodiments, the composition comprises 8 to 15 weight percent of lecithin. In some embodiments, the composition comprises 10 to 15 weight percent of lecithin. In some embodiments, the composition comprises 12 to 15 weight percent of lecithin. In some embodiments, the composition comprises 14 to 15 weight percent of lecithin. In some embodiments, the composition comprises 6 to 13 weight percent of lecithin. In some embodiments, the composition comprises 8 to 10 weight percent of lecithin.

In some embodiments, the lecithin is soy lecithin.

In some embodiments, the composition comprises 0.05 to 1 weight percent of biotin. In some embodiments, the composition comprises 0.05 to 0.8 weight percent of biotin. In some embodiments, the composition comprises 0.05 to 0.6 weight percent of biotin. In some embodiments, the composition comprises 0.05 to 0.4 weight percent of biotin. In some embodiments, the composition comprises 0.05 to 0.2 weight percent of biotin. In some embodiments, the composition comprises 0.1 to 1 weight percent of biotin. In some embodiments, the composition comprises 0.3 to 1 weight percent of biotin. In some embodiments, the composition comprises 0.5 to 1 weight percent of biotin. In some embodiments, the composition comprises 0.7 to 1 weight percent of biotin. In some embodiments, the composition comprises 0.9 to 1 weight percent of biotin.

In some embodiments, the composition comprises 0.1 to 0.8 weight percent of biotin. In some embodiments, the composition comprises 0.3 to 0.6 weight percent of biotin. In some embodiments, the composition comprises 0.4 to 0.5 weight percent of biotin. In some embodiments, the composition comprises 0.05 to 0.08 weight percent of biotin.

In some embodiments, the composition comprises 0.01 to 0.2 weight percent of antioxidant. In some embodiments, the composition comprises 0.01 to 0.15 weight percent of antioxidant. In some embodiments, the composition comprises 0.01 to 0.10 weight percent of antioxidant. In some embodiments, the composition comprises 0.01 to 0.05 weight percent of antioxidant. In some embodiments, the composition comprises 0.05 to 0.15 weight percent of antioxidant. In some embodiments, the composition comprises 0.1 to 0.15 weight percent of antioxidant. In some embodiments, the composition comprises 0.05 to 0.1 weight percent of antioxidant. In some embodiments, the composition comprises 0.01 to 0.03 weight percent of antioxidant.

In some embodiments, the composition comprises folic acid. In some embodiments, the composition comprises 0.01 weight percent to 0.2 weight percent folic acid. In some embodiments, the composition comprises 0.03 weight percent to 0.2 weight percent folic acid. In some embodiments, the composition comprises 0.07 weight percent to 0.2 weight percent folic acid. In some embodiments, the composition comprises 0.1 weight percent to 0.2 weight percent folic acid. In some embodiments, the composition comprises 0.15 weight percent to 0.2 weight percent folic acid. In some embodiments, the composition comprises 0.01 weight percent to 0.15 weight percent folic acid. In some embodiments, the composition comprises 0.01 weight percent to 0.1 weight percent folic acid. In some embodiments, the composition comprises 0.01 weight percent to 0.07 weight percent folic acid. In some embodiments, the composition comprises 0.01 weight percent to 0.05 weight percent folic acid. In some embodiments, the composition comprises 0.05 weight percent to 0.11 weight percent folic acid. In some embodiments, the composition comprises 0.07 weight percent to 0.11 weight percent folic acid.

In some embodiments, the antioxidant is selected from the group consisting of tocopherol, ascorbyl palmitate, Rosemary extract and mixtures thereof.

In some embodiments, the composition comprises additional phospholipid compounds. In some embodiments, the phospholipid compounds comprise phosphatidylinositol (PI), phosphatidic acid (PA), phosphatidylethanolamine (PE), phosphatidylcholine (PC) and combinations thereof.

In some embodiments, the composition comprises emulsifiers. In some embodiments, the composition comprises vitamins.

Figure 1:
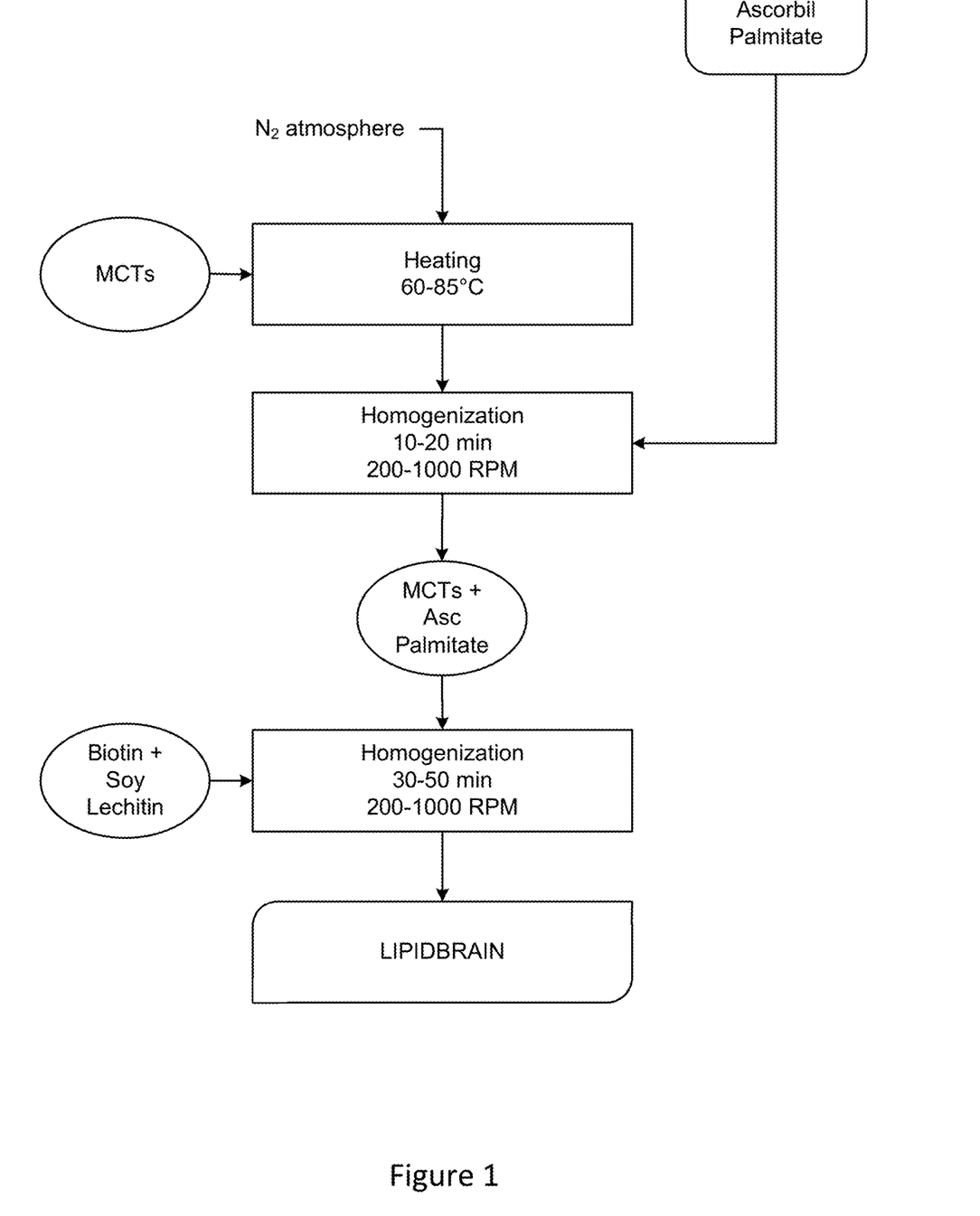
FIG. 1 illustrates a non-limiting method of making embodiments of the present invention.

In some embodiments, the method of making an embodiment of the composition is detailed in FIG. 1. In yet other embodiments, the method of making an embodiment of the composition of the present invention is combining the lipidbrain formed with the process detailed in FIG. 1 with olive oil using any commercially acceptable method of combining lipids.

In other embodiments, the present invention is a method of treatment and/or prevention of cognitive impairment including: orally administering an effective amount per day to a human in need thereof of a composition to improve a clinical dementia rating of the human at least 5% measured after a 12 month duration when compared to a human that is orally administered an identical amount to the effective amount per day of olive oil for a 12 month duration; wherein the composition includes: 75 to 97 weight percent of medium chain triglycerides; wherein the medium chain triglycerides comprise 6 to 12 carbon fatty acid esters of glycerol; and 4 to 15 weight percent of soy lecithin. In embodiments, the composition further includes at least one of: 0.05 to 1 weight percent of biotin or 0.01 to 0.2 weight percent of antioxidant. In yet other embodiments, the composition further includes an antioxidant selected from the group consisting of tocopherol, ascorbyl palmitate, Rosemary extract and mixtures thereof. In some embodiments, the composition is as described in any embodiment detailed herein.

In other embodiments, the present invention is a method of treatment and/or prevention of cognitive impairment including: orally administering an effective amount per day to a human in need thereof of a composition to improve a clinical dementia rating of the human at least 0.8% measured after a 3 month duration when compared to a human that is orally administered an identical amount to the effective amount per day of olive oil for a 3 month duration; wherein the composition includes: 75 to 97 weight percent of medium chain triglycerides; wherein the medium chain triglycerides comprise 6 to 12 carbon fatty acid esters of glycerol; and 4 to 15 weight percent of soy lecithin. In embodiments, the composition further includes at least one of: 0.05 to 1 weight percent of biotin or 0.01 to 0.2 weight percent of antioxidant. In yet other embodiments, the composition further includes an antioxidant selected from the group consisting of tocopherol, ascorbyl palmitate, Rosemary extract and mixtures thereof. In some embodiments, the composition is as described in any embodiment detailed herein.

In some embodiments, the cognitive impairment is a result of a neurological disease. In some embodiments, the cognitive impairment is a result of Aβ toxicity. In some embodiments, the cognitive impairment is a result of a progressive cognitive disorder including, but not limited to, Very Mild Dementia, Mild Dementia, Moderate Dementia, Severe Dementia, Alzheimer's Disease, progressive supranuclear palsy; a dementia; Creutzfeldt-Jacob disease, frontotemporal dementia, Pick's disease, Frontotemporal Dementia with Parkinsonism-17 corticobasal degeneration, frontotemporal lobe degeneration; Huntington's Disease; or Parkinson's Disease.

In some embodiments, the effective amount comprises 5 grams to 100 grams of the composition per day. In some embodiments, the effective amount comprises 5 grams to 100 grams of the composition per day. In some embodiments, the effective amount comprises 15 grams to 100 grams of the composition per day. In some embodiments, the effective amount comprises 25 grams to 100 grams of the composition per day. In some embodiments, the effective amount comprises 40 grams to 100 grams of the composition per day. In some embodiments, the effective amount comprises 50 grams to 100 grams of the composition per day. In some embodiments, the effective amount comprises 65 grams to 100 grams of the composition per day. In some embodiments, the effective amount comprises 75 grams to 100 grams of the composition per day. In some embodiments, the effective amount comprises 85 grams to 100 grams of the composition per day. In some embodiments, the effective amount comprises 95 grams to 100 grams of the composition per day.

In some embodiments, the effective amount comprises at least 5 grams of the composition per day. In some embodiments, the effective amount comprises at least 15 grams of the composition per day. In some embodiments, the effective amount comprises at least 25 grams of the composition per day. In some embodiments, the effective amount comprises at least 40 grams of the composition per day. In some embodiments, the effective amount comprises at least 50 grams of the composition per day. In some embodiments, the effective amount comprises at least 75 grams of the composition per day. In some embodiments, the effective amount comprises at least 85 grams of the composition per day. In some embodiments, the effective amount comprises at least 95 grams of the composition per day. In some embodiments, the effective amount comprises at least 100 grams of the composition per day.

In some embodiments, the effective amount comprises 5 grams to 90 grams of the composition per day. In some embodiments, the effective amount comprises 5 grams to 70 grams of the composition per day. In some embodiments, the effective amount comprises 5 grams to 50 grams of the composition per day. In some embodiments, the effective amount comprises 5 grams to 40 grams of the composition per day. In some embodiments, the effective amount comprises 5 grams to 25 grams of the composition per day. In some embodiments, the effective amount comprises 5 grams to 15 grams of the composition per day. In some embodiments, the effective amount comprises 5 grams to 100 grams of the composition per day.

In some embodiments, the effective amount comprises 25 grams to 75 grams of the composition per day. In some embodiments, the effective amount comprises 35 grams to 80 grams of the composition per day. In some embodiments, the effective amount comprises 40 grams to 60 grams of the composition per day. In some embodiments, the effective amount comprises 50 grams of the composition per day.

In embodiments, the effective amount of the composition is based, at least in part, on the weight of the human in need thereof.

In other embodiments, the effective amount comprises 15 to 25 grams per dose and two to four doses per day. In embodiments, the effective amount comprises 15 to 25 grams per dose and two doses per day. In other embodiments, the effective amount comprises 15 to 25 grams per dose and three doses per day. In other embodiments, the effective amount comprises 15 to 25 grams per dose and four doses per day.

In embodiments, the effective amount comprises 15 grams per dose and three doses per day. In embodiments, the effective amount comprises 15 grams per dose and four doses per day.

In embodiments, the effective amount comprises 17 grams per dose and three doses per day.

In other embodiments, the present invention is a method of treatment and/or prevention of cognitive impairment comprising: orally administering an effective amount per day to a human in need thereof of a composition to improve a clinical dementia rating of the human at least 25% measured after a 12 month duration when compared to a human that is orally administered an identical amount to the effective amount per day of olive oil for a 12 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil. In embodiments, the composition further includes at least one of: 0.05 to 1 weight percent of biotin or 0.01 to 0.2 weight percent of antioxidant. In yet other embodiments, the composition further includes an antioxidant selected from the group consisting of tocopherol, ascorbyl palmitate, Rosemary extract and mixtures thereof. In some embodiments, the composition is as described in any embodiment detailed herein.

In other embodiments, the present invention is a method of treatment and/or prevention of cognitive impairment comprising: orally administering an effective amount per day to a human in need thereof of a composition to improve a clinical dementia rating of the human at least 20% measured after a 12 month duration when compared to a human that is orally administered an identical amount to the effective amount per day of olive oil for a 12 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil. In other embodiments, the present invention is a method of treatment and/or prevention of cognitive impairment comprising: orally administering an effective amount per day to a human in need thereof of a composition to improve a clinical dementia rating of the human at least 15% measured after a 12 month duration when compared to a human that is orally administered an identical amount to the effective amount per day of olive oil for a 12 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil.

In other embodiments, the present invention is a method of treatment and/or prevention of cognitive impairment comprising: orally administering an effective amount per day to a human in need thereof of a composition to improve a clinical dementia rating of the human at least 10% measured after a 12 month duration when compared to a human that is orally administered an identical amount to the effective amount per day of olive oil for a 12 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil. In other embodiments, the present invention is a method of treatment and/or prevention of cognitive impairment comprising: orally administering an effective amount per day to a human in need thereof of a composition to improve a clinical dementia rating of the human at least 5% measured after a 12 month duration when compared to a human that is orally administered an identical amount to the effective amount per day of olive oil for a 12 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil.

In other embodiments, the present invention is a method of treatment and/or prevention of cognitive impairment comprising: orally administering an effective amount per day to a human in need thereof of a composition to improve a clinical dementia rating of the human at least 5% measured after a 3 month duration when compared to a human that is orally administered an identical amount to the effective amount per day of olive oil for a 3 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil. In other embodiments, the present invention is a method of treatment and/or prevention of cognitive impairment comprising: orally administering an effective amount per day to a human in need thereof of a composition to improve a clinical dementia rating of the human at least 8% measured after a 3 month duration when compared to a human that is orally administered an identical amount to the effective amount per day of olive oil for a 3 month duration; wherein the composition comprises: a first component comprising: 75 to 97 weight percent of medium chain triglycerides; wherein the medium chain triglycerides comprise 6 to 12 carbon fatty acid esters of glycerol; 4 to 15 weight percent of soy lecithin; and olive oil.

In some embodiments, the cognitive impairment is a result of a neurological disease. In some embodiments, the cognitive impairment is a result of Aβ toxicity. In some embodiments, the cognitive impairment is a result of a progressive cognitive disorder including, but not limited to, Very Mild Dementia, Mild Dementia, Moderate Dementia, Severe Dementia, Alzheimer's Disease, progressive supranuclear palsy; a dementia; Creutzfeldt-Jacob disease, frontotemporal dementia, Pick's disease, Frontotemporal Dementia with Parkinsonism-17 corticobasal degeneration, frontotemporal lobe degeneration; Huntington's Disease; or Parkinson's Disease.

In embodiments, a weight ratio of the first component to the olive oil in the composition is 5:1 to 1:5. In embodiments, a weight ratio of the first component to the olive oil in the composition is 4:1 to 1:4. In embodiments, a weight ratio of the first component to the olive oil in the composition is 3:1 to 1:3. In embodiments, a weight ratio of the first component to the olive oil in the composition is 2:1 to 1:2. In embodiments, a weight ratio of the first component to the olive oil in the composition is 1:1.

In some embodiments, the effective amount comprises 5 grams to 100 grams of the composition having a weight ratio of the first component to the olive oil of 2:1 to 1:2 per day. In some embodiments, the effective amount comprises 5 grams to 100 grams of the composition having a weight ratio of the first component to the olive oil of 2:1 to 1:2 per day. In some embodiments, the effective amount comprises 15 grams to 100 grams of the composition having a weight ratio of the first component to the olive oil of 2:1 to 1:2 per day. In some embodiments, the effective amount comprises 25 grams to 100 grams of the composition having a weight ratio of the first component to the olive oil of 2:1 to 1:2 per day. In some embodiments, the effective amount comprises 40 grams to 100 grams of the composition per day. In some embodiments, the effective amount comprises 50 grams to 100 grams of the composition having a weight ratio of the first component to the olive oil of 2:1 to 1:2 per day. In some embodiments, the effective amount comprises 65 grams to 100 grams of the composition having a weight ratio of the first component to the olive oil of 2:1 to 1:2 per day. In some embodiments, the effective amount comprises 75 grams to 100 grams of the composition having a weight ratio of the first component to the olive oil of 2:1 to 1:2 per day. In some embodiments, the effective amount comprises 85 grams to 100 grams of the composition having a weight ratio of the first component to the olive oil of 2:1 to 1:2 per day. In some embodiments, the effective amount comprises 95 grams to 100 grams of the composition having a weight ratio of the first component to the olive oil of 2:1 to 1:2 per day.

In some embodiments, the effective amount comprises at least 5 grams of the composition having a weight ratio of the first component to the olive oil of 2:1 to 1:2 per day. In some embodiments, the effective amount comprises at least 15 grams of the composition having a weight ratio of the first component to the olive oil of 2:1 to 1:2 per day. In some embodiments, the effective amount comprises at least 25 grams of the composition having a weight ratio of the first component to the olive oil of 2:1 to 1:2 per day. In some embodiments, the effective amount comprises at least 40 grams of the composition having a weight ratio of the first component to the olive oil of 2:1 to 1:2 per day. In some embodiments, the effective amount comprises at least 50 grams of the composition having a weight ratio of the first component to the olive oil of 2:1 to 1:2 per day. In some embodiments, the effective amount comprises at least 75 grams of the composition having a weight ratio of the first component to the olive oil of 2:1 to 1:2 per day. In some embodiments, the effective amount comprises at least 85 grams of the composition having a weight ratio of the first component to the olive oil of 2:1 to 1:2 per day. In some embodiments, the effective amount comprises at least 95 grams of the composition having a weight ratio of the first component to the olive oil of 2:1 to 1:2 per day. In some embodiments, the effective amount comprises at least 100 grams of the composition having a weight ratio of the first component to the olive oil of 2:1 to 1:2 per day.

In some embodiments, the effective amount comprises 5 grams to 90 grams of the composition having a weight ratio of the first component to the olive oil of 2:1 to 1:2 per day. In some embodiments, the effective amount comprises 5 grams to 70 grams of the composition having a weight ratio of the first component to the olive oil of 2:1 to 1:2 per day. In some embodiments, the effective amount comprises 5 grams to 50 grams of the composition having a weight ratio of the first component to the olive oil of 2:1 to 1:2 per day. In some embodiments, the effective amount comprises 5 grams to 40 grams of the composition having a weight ratio of the first component to the olive oil of 2:1 to 1:2 per day. In some embodiments, the effective amount comprises 5 grams to 25 grams of the composition having a weight ratio of the first component to the olive oil of 2:1 to 1:2 per day. In some embodiments, the effective amount comprises 5 grams to 15 grams of the composition having a weight ratio of the first component to the olive oil of 2:1 to 1:2 per day. In some embodiments, the effective amount comprises 5 grams to 100 grams of the composition having a weight ratio of the first component to the olive oil of 2:1 to 1:2 per day.

In some embodiments, the effective amount comprises 25 grams to 75 grams of the composition having a weight ratio of the first component to the olive oil of 2:1 to 1:2 per day. In some embodiments, the effective amount comprises 35 grams to 80 grams of the composition having a weight ratio of the first component to the olive oil of 2:1 to 1:2 per day. In some embodiments, the effective amount comprises 40 grams to 60 grams of the composition having a weight ratio of the first component to the olive oil of 2:1 to 1:2 per day. In some embodiments, the effective amount comprises 50 grams of the composition having a weight ratio of the first component to the olive oil of 2:1 to 1:2 per day. In some embodiments, the effective amount comprises 50 grams of the composition having a weight ratio of the first component to the olive oil of 1:1 per day.

In some embodiments, the olive oil in the composition detailed in one or more embodiments herein, may be replaced, at least in part, by flax seed oil, high oleic palm oil or high oleic sunflower oil, where said oils are virgin and obtained by cold pressing.

In embodiments, the effective amount of the composition is based, at least in part, on the weight of the human in need thereof.

In other embodiments, the effective amount comprises 15 to 25 grams per dose and two to four doses per day. In embodiments, the effective amount comprises 15 to 25 grams per dose and two doses per day. In other embodiments, the effective amount comprises 15 to 25 grams per dose and three doses per day. In other embodiments, the effective amount comprises 15 to 25 grams per dose and four doses per day.

In embodiments, the effective amount comprises 15 grams per dose and three doses per day. In embodiments, the effective amount comprises 15 grams per dose and four doses per day.

In embodiments, the effective amount comprises 17 grams per dose and three doses per day.

In some embodiments, the effective amount comprises any dosage amount detailed above and one to three doses per day. In some embodiments, the effective amount comprises any dosage amount detailed above and one to two doses per day. In some embodiments, the effective amount comprises any dosage amount detailed above and one dose per day. In some embodiments, the effective amount comprises any dosage amount detailed above and two doses per day. In some embodiments, the effective amount comprises any dosage amount detailed above and three doses per day. In some embodiments, the effective amount comprises any dosage amount detailed above and four doses per day.

In some embodiments, the present invention is a solid powder composition comprising: a first component comprising: 75 to 97 weight percent of medium chain triglycerides; wherein the medium chain triglycerides comprise fatty acid esters of glycerol of 6 to 12 carbon atoms; 4 to 15 weight percent soy lecithin; and olive oil.

In embodiments, the solid powder composition further includes at least one of: 0.05 to 1 weight percent biotin or 0.01 to 0.2 weight percent antioxidant. In still other embodiments, the solid powder composition further includes an antioxidant selected from the group consisting of tocopherol, ascorbyl palmitate, rosemary extract and mixtures thereof. In still other embodiments, the solid powder composition further includes 0.05 weight percent to 0.1 weight percent pyridoxine and/or cobalamin.

In embodiments, a weight ratio of the first component to olive oil in the solid powder composition is from 5:1 to 1:5. In embodiments, a weight ratio of the first component to olive oil in the solid powder composition is from 4:1 to 1:4. In embodiments, a weight ratio of the first component to olive oil in the composition is from 3:1 to 1:3. In embodiments, a weight ratio of the first component to olive oil in the solid composition is from 2:1 to 1:2. In embodiments, a weight ratio of the first component to olive oil in the solid composition is 1:1.

In embodiments, the solid powder composition further includes maltodextrin in a concentration of 0% to 20%, sugar in a concentration of 0% to 30%, whey in a concentration of 0% to 10%, caseinate in a concentration of 0% to 6%, corn starch in a concentration of 0% to 4%, soy lecithin in a concentration of 0% to 3%, gum arabic in a concentration of 0% to 1.5%, sodium carboxymethyl cellulose in a concentration of 0% to 1%, premix of vitamins and minerals in a concentration of 0.05% to 3%, stevia in a concentration of 0% to 0.08%, flavorings, and/or Natural antioxidants (tocopherols) in a concentration of 0% to 0.04%.

In some embodiments, the method for making an embodiment of the composition is detailed in FIG. 1. In still other embodiments, the method for making an embodiment of the composition of the present invention is to combine the lipidbrain formed with the process detailed in the FIG. 1 with olive oil using any commercially acceptable method to combine lipids. In yet another embodiment, the method for making an embodiment of the solid composition of the present invention is to combine the lipidbrain formed with the process detailed in FIG. 1 with olive oil using any commercially acceptable method for combining lipids, followed by a process of spray-drying and microencapsulation by the application of the methodologies known to the person skilled in the art Traditionally, there are two methods to assess the improvement and/or prevention of neurodegenerative disease. A first method is related to the phenotype of cognitive impairment and the second method is based on genotype associate with this cognitive impairment.

A first method is based on a method of psychiatric criteria according to American Psychiatric Association. In this method, DSM-IV and classification of mental and behavioral disorders of World Health Organization ICD-10, cognitive decay is diagnosed in accordance with the following four criteria:

I. Impairment of one or more of the following cognitive areas:
  a. Attention/concentration
  b. Language
  c. Gnosia
  d. Praxis
  e. Visuospatial abilities
  f. Executive function II. The cognitive impairment is:
  a. Acquired, indicating a decline over previous capabilities of the individual;
  b. Reported by the patient or a reliable informant;
  c. Focused on neuropsychological examination; and
  d. Several months and observed in patients with a normal level of consciousness III. The cognitive impairment only interferes minimally in basal or advanced activities of daily living; and.

IV. Cognitive impairment is not associated with disorders at conscience level.

According to the criteria described above there is an ascending classification of: Mild cognitive impairment, combined Dementia, probable Alzheimer's Disease, possible Alzheimer's Disease, Alzheimer's Disease and confirmed Alzheimer's Disease with associated cerebrovascular disease: An improvement in cognitive impairment is evident at two levels: i) when any of these criteria (ex. concentration, memory, praxis, etc.) evolve positively; ii) the disease suffers a stage change to a minor stage (ex. combined dementia with mild cognitive impairment).

A second method is a genetic markers method. In the second method, DNA extracted from blood plasma allows the assessment of genetic variants associated to the production of proteins that regulate the neuropathological changes caused by neurodegenerative disease. A decrease in the expression of these genes is directly related to cognitive enhancement.

As used herein, "CDR" is used to assess the treatment of cognitive impairment.

Non-Limiting Examples

The following examples are intended to illustrate the invention and should not be construed as limiting the invention in any way.

Trials consisted in growing transgenic *Caenorhabditis elegans* strain CL4176 at 16° C. and synchronized age with two different doses, 1 and 10 mg/mL, of the lipid blends: Lipid Brain and Control Z (negative control). The compositions of Lipid Brain and Control Z are detailed in Tables 2 and 3.

TABLE 2

| LIPID BRAIN | |
| --- | --- |
| Raw Material | wt % |
| Medium Chain Triglycerides (MCTs) | 93.24 |
| Soy Lecithin | 6.67 |
| Biotin | 0.07 |
| Ascorbil Palmitate | 0.02 |

TABLE 3

| CONTROL Z | |
|---|---|
| Raw Material | wt % |
| Soybean Oil | 69.988 |
| Palm Olein | 30.00 |
| TBHQ | 0.012 |

Once the nematodes reached the larval stage L3, Aβ13 peptide expression was induced by increasing the temperature to 25° C. After induction, paralysis was count on each population until 100% were paralyzed. The tests included control nematodes maintained at 16° C. (Aβ peptide expression is not induced), a teed control condition (NG induction medium) and a positive control (extract from Gingko biloba) condition. The curves obtained were analyzed statistically using the software Graph Pad Prism.

Figure 2:
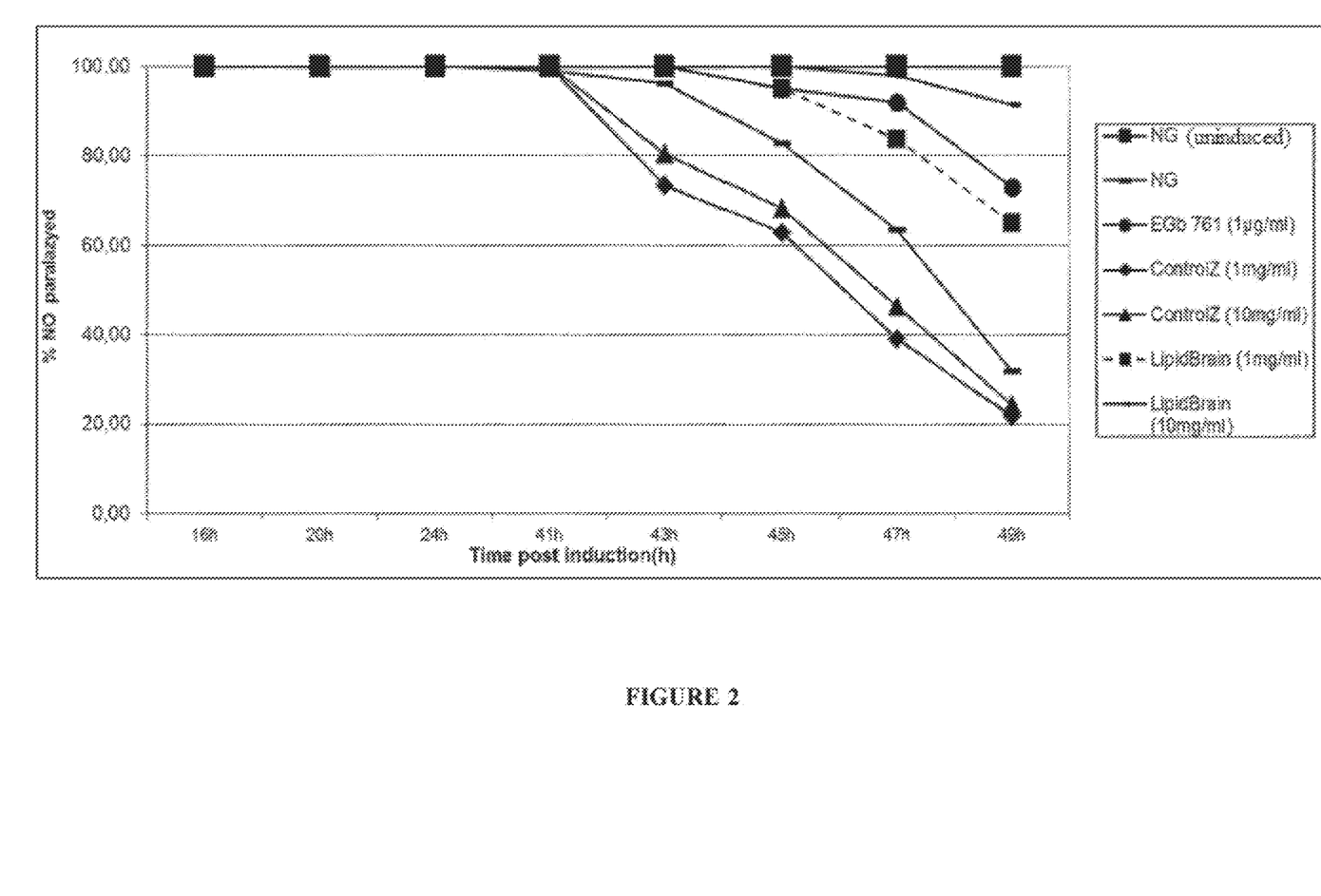
FIG. 2 illustrates the results a nematode study of embodiments of the present invention.

The averaged results are shown in FIG. 2. In the non-limiting example, the effect of Lipid Brain and Control Z's blends on body paralysis induced in *Caenorhabditis elegans* strain CL4176 is shown in FIG. 2. The figure represents the percentage of non-paralyzed nematodes in each condition versus time. Paralysis curves obtained indicated a significant protective effect with Lipid Brain at two concentrations tested as compared to the NG. Furthermore, the effect was dose dependent, increasing sample concentration show delay in the paralysis acquisition. The dose of 10 mg/mL delayed significantly the appearance of body paralysis, demonstrating the Lipid Brain effect on reducing of the peptide-induced toxicity. Additionally, this effect was greater than the obtained with the Ginkgobiloba extract EGb 761 (positive control) and the NG.

Moreover, no positive effect was shown with the Control Z compared to the NG, and both doses tested resulted in curves similar in paralysis. All these results are corroborated with statistical analysis performed with the GraphPad Prism program as detailed in Table 4.

The data indicated that in control conditions (NG) worm paralysis began at 41 h. Although the Control Z shows delayed entry into paralysis (43 h), supplementation with the Control Z had no positive effects on paralysis. Lipid Brain, however, had a protective effect at doses of 1 mg/mL (P=0.006) and 10 mg/mL (P<0.0001) and showed a delay in the entry into paralysis (47 h).

TABLE 4

| Condition | Paralysis initial time (h) | Log Rank Test X² | P-value | Protective Effect |
|---|---|---|---|---|
| NG | 41 | | | |
| EGb 761 (1 µg/mL) | 45 | 26.83 | <0.0001 | Yes |
| Control Z (1 mg/mL) | 43 | 8.85 | 0.0029 | No |
| Control Z (10 mg/mL) | 43 | 9.98 | 0.0016 | No |
| Lipid Brain (1 mg/mL) | 43 | 7.5 | 0.006 | Yes |
| Lipid Brain (10 mg/mL) | 47 | 69.19 | <0.0001 | Yes |

The results of the non-limiting examples show the effectiveness of Lipid Brain on reducing body paralysis in the transgenic *Caenorhabditis elegans* strain CL4176. *Caenorhabditis elegans* is a pre-clinical model for determining the neuromolecular basis of cognitive function. *Caenorhabditis eiegans* has been used to model aspects of a different number of age-associated neurodegenerative diseases, including Alzheimer's, Parkinson's and Huntington's diseases. These models typically involve a transgenic expression of disease-associated human proteins. Thus, since this model of Alzheimer accumulation can be correlated with toxicity Aβ peptide, the results of this study indicate that the administration of the Lipid Brain reduces toxicity in transgenic strain and thus, would be expected to result in a "reduced rate of onset or magnitude of cognitive impairment."

A human study was further conducted to evaluate the effect of an embodiment of a lipid composition of the present invention. The purpose of the study is to evaluate the effect of an embodiment of a lipid composition of the present invention on 110 patients diagnosed with cognitive impairment or mild-to-moderate Alzheimer's disease. Study parameters: randomized, double blind, placebo-controlled prospective.

Table 5 below illustrates the compositions and treatment regimen of the study.

TABLE 5

| Sample | Treatment Regimen |
|---|---|
| Sample 1 Glass bottle with 25 grams Lipidbrai (described in Table 2) and 25 grams Olive Oil. | Daily intake of one bottle containing Sample 1 |
| Sample 2 Glass bottle with 50 grams Lipidbrain (described in Table 2) | Daily intake of one bottle containing Sample 2 |
| Comparative Sample 3 Glass bottle with 50 grams of Olive oil | Daily intake of one bottle containing Comparative Sample 3 |

The density of the Sample 1, Sample 2 and Comparative Sample 3 is 9 milligrams per milliliter. The specifications of the olive oil used in Sample 1 and Comparative Sample 3 are detailed in FIGS. 4 to 7.

The targets of the study include the following:

Changes in Clinical Dementia Rating (CDR) over a timeframe of 3 months, 6 months and 12 months, and The patient eligibility guidelines for the study are detailed in Table 6.

TABLE 6

| | |
|---|---|
| Minimum Age | 55 Years |
| Maximum Age | 85 Years |
| Gender | Both |
| Healthy Volunteers | No |
| Inclusion Criteria | Informed consents signed by patients and/or caretaker The patient has to fulfill dementia clinical criteria. MMSE score between 18 and 26. |

TABLE 6-continued

| | |
|---|---|
| | The patient can fulfill all neuropsychologic test, according to investigator.<br>The patient has to be always with his/her caretaker during monitorization visits<br>The caretaker has to be in regular contact with the patient, knowing his/her situation and participation in the study.<br>The caretaker has to check four times per week, at least, the product intake, as well as the routine medication and his/her dietetic habits.<br>Both caretaker and patient have to be able to complete the product intake during all the length of the study, according to |
| Exclusion Criteria: | Patient and/or caretaker not being able to understand and agree in writing their participation in the study.<br>Patient disability to oral intake of products.<br>Known allergy to any of the product components (active and placebo)<br>Evidence of suffering other neuropsychiatric disturbances apart of dementia as: Parkinson disease, psychotic disturbance, bipolar depression.<br>Regular intake of alcohol higher than 45 g ethanol/day, during the year before study inclusion.<br>Any known concurrent malignant pathology in the moment of study inclusion, or severe metabolic, cardiovascular, renal, hepatic, or gastrointestinal disease that cannot allow the ending of the study according the investigator.<br>Any analytical abnormality during the screening, apart from: Creatinine no less than 1.7 mg/dL; low levels of Vitamin B12, and TSH abnormal values |

The magnitude of the treatment effect (as percentage) was calculated by the difference between the actual values (in the corresponding 95% confidence interval) from the baseline (which indicates that the treatment had no effect). This magnitude represents percentage of improvement through CDR value. These calculations and results are shown in Table 7 and FIG. 3.

TABLE 7

Figure 3:
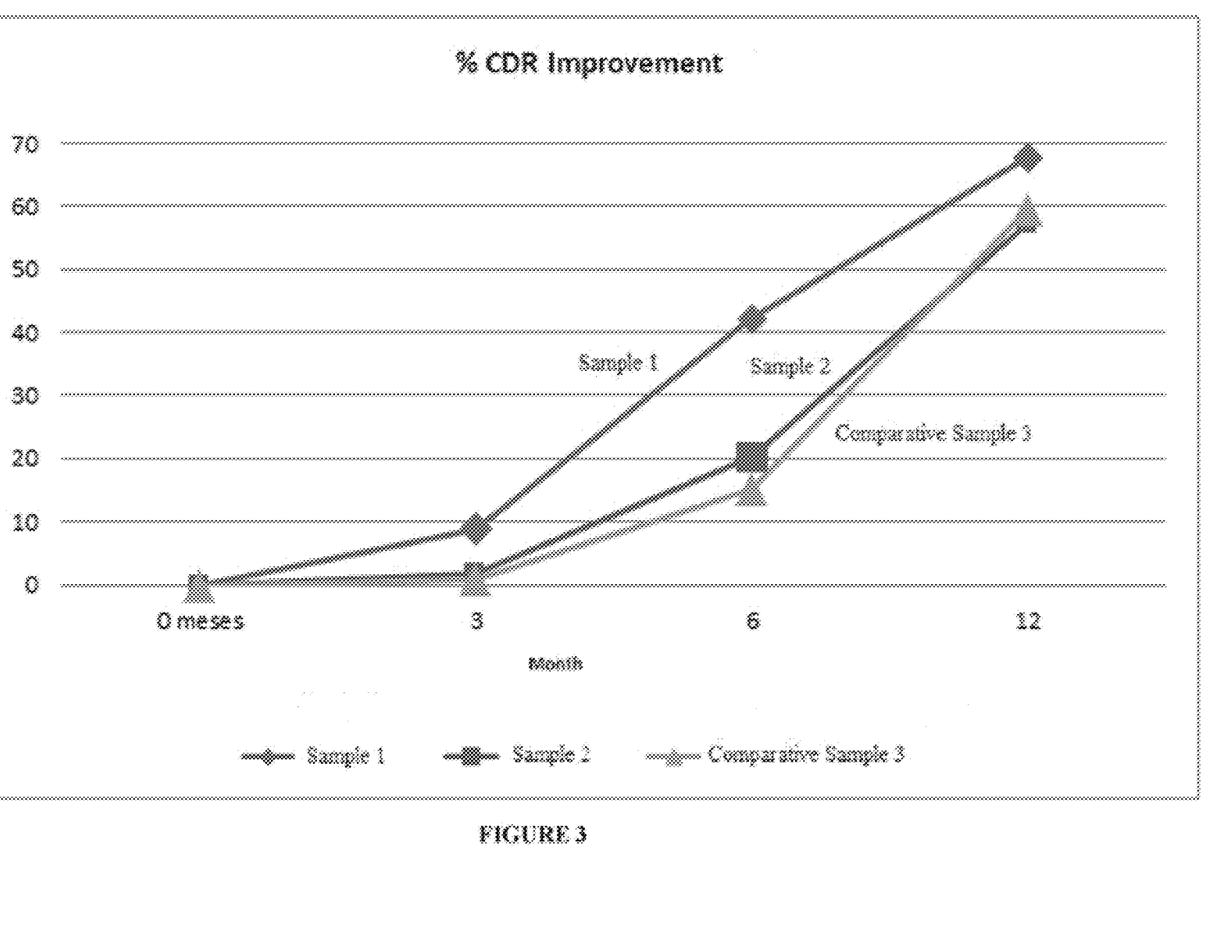
FIG. 3 illustrates the results of a human study of embodiments of the present invention.
Figure 4:
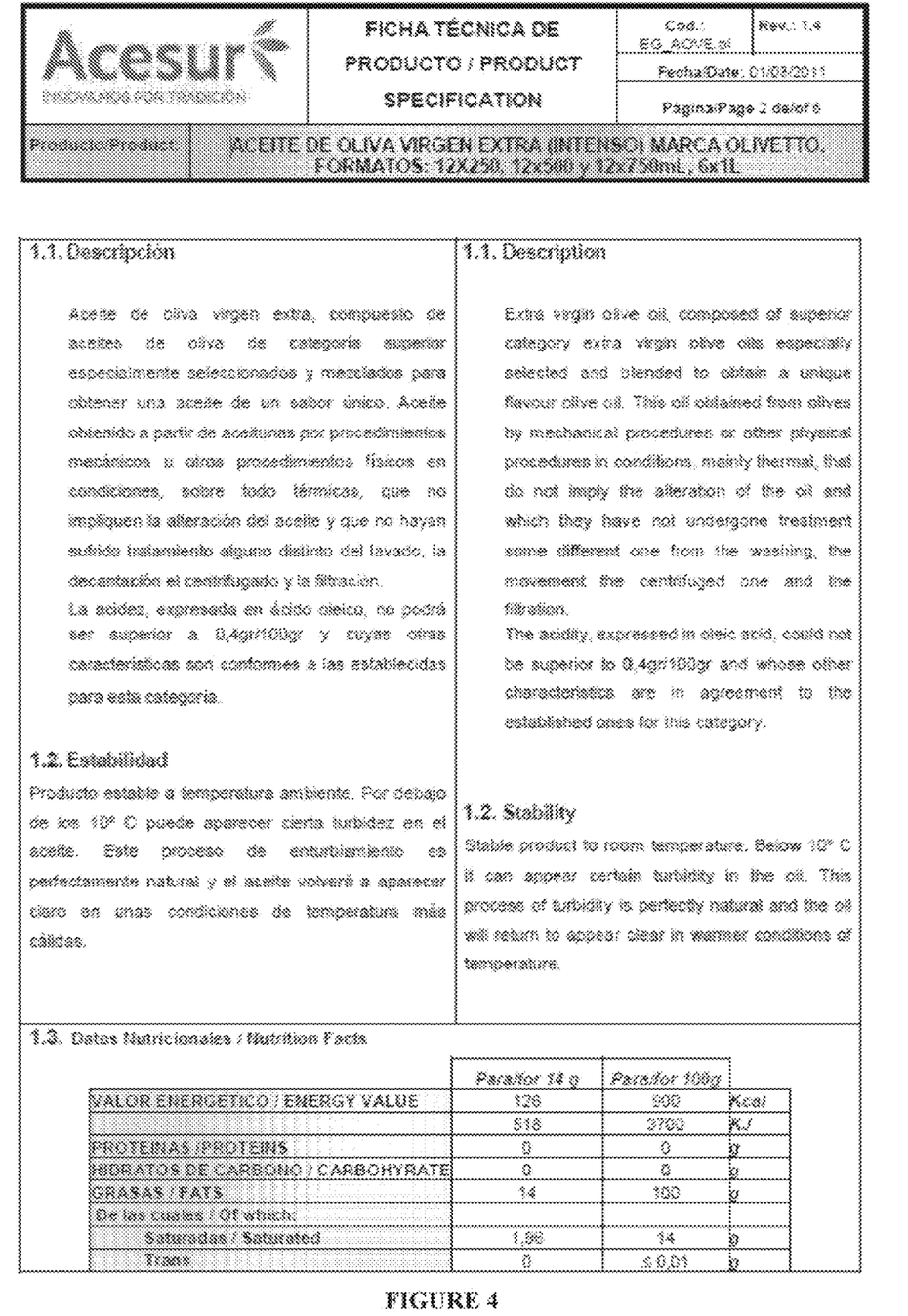
FIG. 4 illustrates the specifications of olive oil used in the human study.
Figure 5:
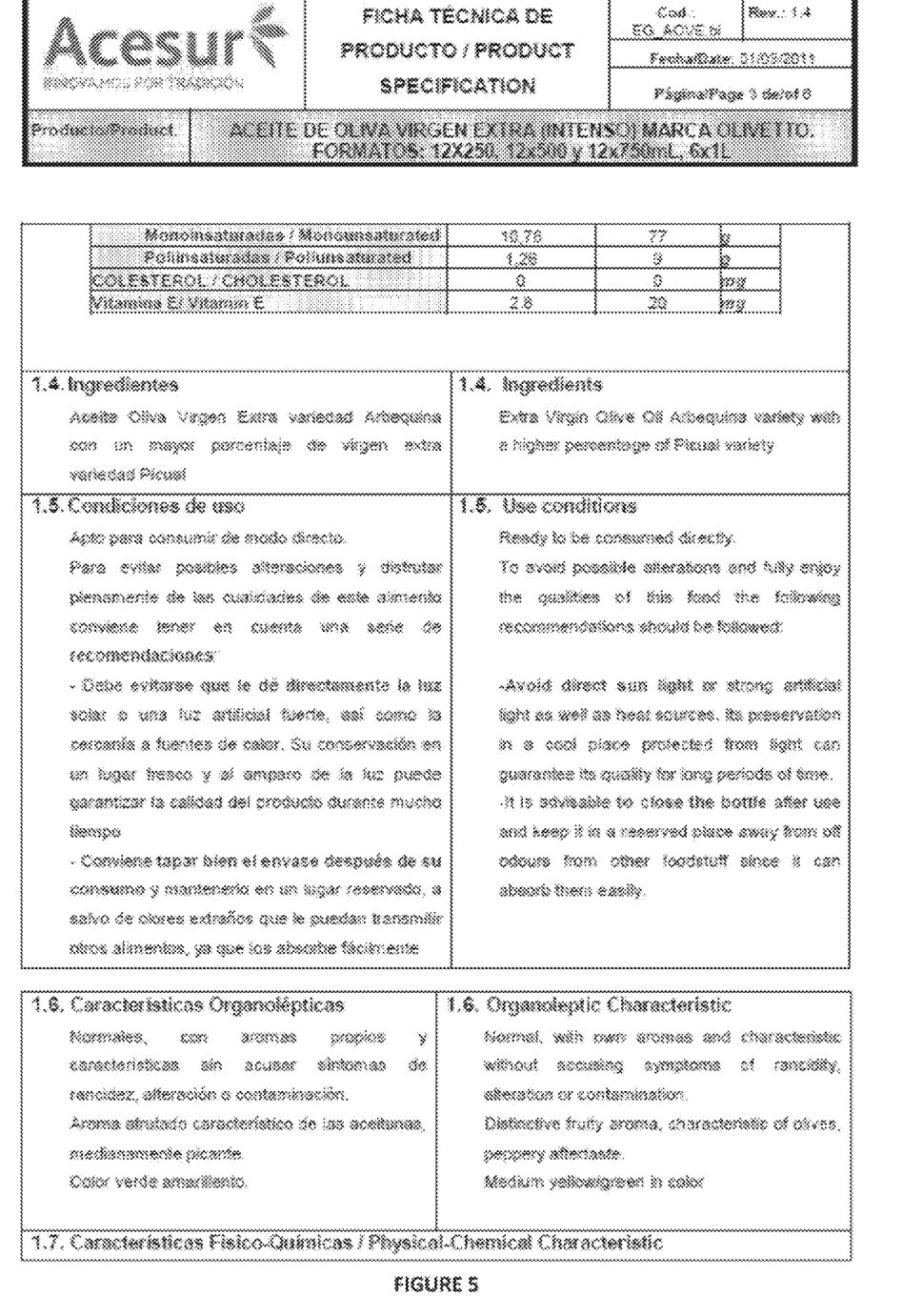
FIG. 5 illustrates the specifications of olive oil used in the human study.
Figure 6:
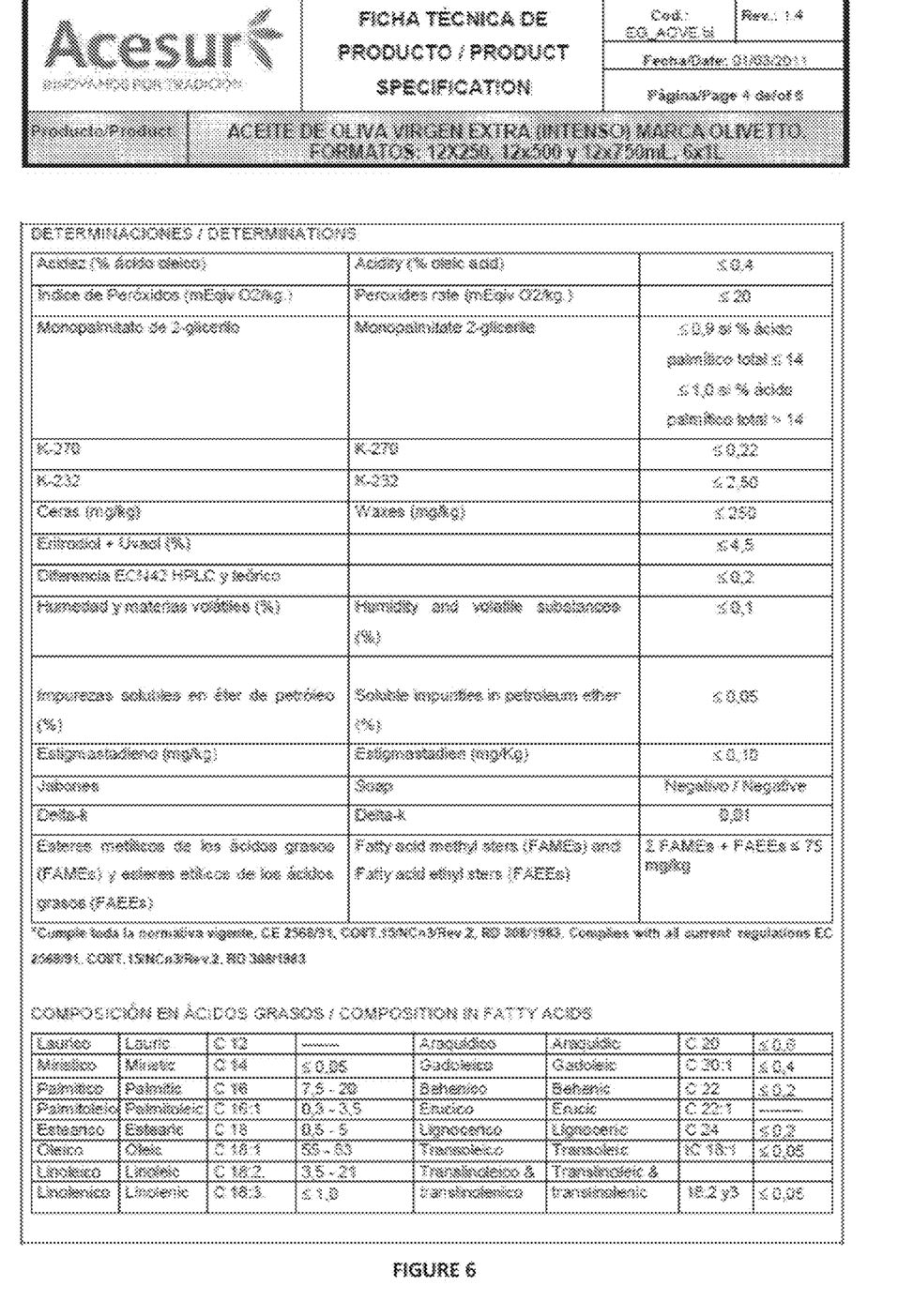
FIG. 6 illustrates the specifications of olive oil used in the human study.
Figure 7:
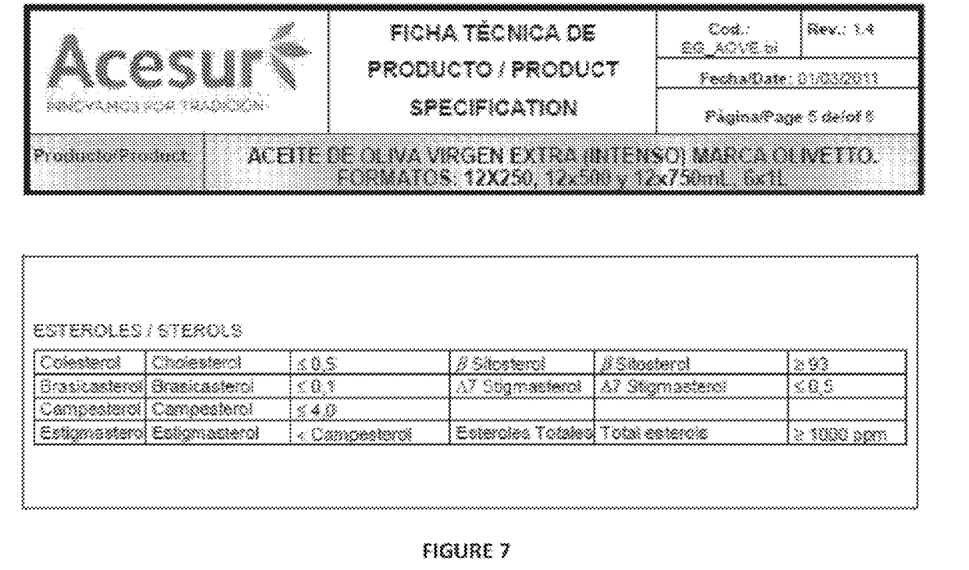
FIG. 7 illustrates the specifications of olive oil used in the human study.

| | % CDR Improvement | | | |
|---|---|---|---|---|
| Composition | 0 months | 3 months | 6 months | 12 months |
| Sample 1 | 0 | 8.87 | 42.11 | 67.7 |
| Sample 2 | 0 | 1.66 | 20.23 | 57.1 |
| Comparative Sample | 0 | 0.8 | 15.29 | 59.3 |

According to % CDR improvement, patients taking Sample 1 exhibited an increase in the % CDR improvement values in comparison to Sample 2 and Comparative Sample 3. The results illustrate the benefits of an embodiment of the lipidic blend of the present invention, alone and in combination with olive oil, in treatment of cognitive impairment compared to olive oil alone.

Moreover, the CDR correlates and quantifies the level of memory of the patients. Additionally, the inventors expect that the effect of improved CDR will also result in a long term impact on a change in the Mini Mental State Examination (MMSE) and biomarkers in blood. The MMSE is a tool that can be used to systematically and thoroughly assess mental status. The MMSE is an 11-question measure that tests five areas of cognitive function: orientation, registration, attention and calculation, recall, and language. The maximum score is 30. A score of 23 or lower is indicative of cognitive impairment. The MMSE takes 5-10 minutes to administer.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

The invention claimed is:

1. An emulsion consisting essentially of:
 (i) 75 to 97 weight percent of medium chain triglycerides; wherein the medium chain triglycerides consist essentially of 6 to 12 carbon fatty acid esters of glycerol and the fatty acids are selected from the group consisting of caproic, caprylic, capric, lauric acid and mixtures thereof;
 (ii) 4 to 15 weight percent of soy lecithin;
 (iii) 0.05 to 1 weight percent of biotin; and
 (iv) 0.01 to 0.2 weight percent of antioxidant, wherein the antioxidant is selected from the group consisting of tocopherol, ascorbyl palmitate, Rosemary extract and mixtures thereof.

2. The emulsion of claim 1, wherein the emulsion consists essentially of:
 85 to 97 weight percent of the medium chain triglycerides, 8 to 15 weight percent of the soy lecithin, 1 weight percent of the biotin, and 0.1 to 0.2 weight percent of the antioxidant.

3. The emulsion of claim 1, wherein the emulsion consists essentially of:
 (i) 85 to 97 weight percent of medium chain triglycerides; wherein the medium chain triglycerides consist essentially of 6 to 12 carbon fatty acid esters of glycerol;
 (ii) 5 to 10 weight percent of soy lecithin;
 (iii) 0.05 to 0.2 weight percent of biotin; and
 (iv) 0.01 to 0.2 weight percent of antioxidant, wherein the antioxidant is selected from the group consisting of tocopherol, ascorbyl palmitate, Rosemary extract and mixtures thereof.

4. An emulsion, consisting essentially of:
 (a) a first component consisting essentially of:
  (i) 75 to 97 weight percent of medium chain triglycerides;

wherein the medium chain triglycerides consist essentially of 6 to 12 carbon fatty acid esters of glycerol and the fatty acids are selected from the group consisting of caproic, caprylic, capric, lauric acid and mixtures thereof;
(ii) 4 to 15 weight percent of soy lecithin;
(iii) 0.05 to 1 weight percent biotin; and
(iv) 0.01 to 0.2 weight percent antioxidant, wherein the antioxidant is selected from the group consisting of tocopherol, ascorbyl palmitate, rosemary extract and mixtures thereof; and
(b) olive oil, wherein a weight ratio of the first component to the olive oil is 2:1 to 1:2 and the olive oil.

\* \* \* \* \*